United States Patent [19]
Jiricny et al.

[11] Patent Number: 4,950,366
[45] Date of Patent: Aug. 21, 1990

[54] METHOD OF PRODUCTION OF D-ARABINOSE

[75] Inventors: Vladimír Jiřičny; Vladimír Staněk; Magda Borovcová, all of Prague, Czechoslovakia

[73] Assignee: Ceskoslovenska akademie ved Praha, Prague, Czechoslovakia

[21] Appl. No.: 267,228

[22] Filed: Nov. 4, 1988

[30] Foreign Application Priority Data

Dec. 3, 1987 [CS] Czechoslovakia ............ 8822-87

[51] Int. Cl.$^5$ ........................... C25B 3/00
[52] U.S. Cl. .................... 204/59 R; 204/78; 204/79; 204/80
[58] Field of Search ............ 204/78, 79, 80, 59 R

[56] References Cited

U.S. PATENT DOCUMENTS

| | | | |
|---|---|---|---|
| 4,004,994 | 1/1977 | Andrus | 204/149 |
| 4,206,020 | 6/1980 | Backhurst et al. | 204/78 |
| 4,778,531 | 10/1988 | Dobler et al. | 204/186 |

OTHER PUBLICATIONS

Chemical Abstract 99:5966 y, Noguchi, vol 99, No. 1, Jul. 4, 1983, p. 548.
Chemical Abstract 103:78230g, Park et al., vol. 103, No. 10, Sep. 9, 1985, p. 464.
Hay, G. W. et al., "Electrolysis of Low Molecular Weight Carbohydrates in Non-Aqueous Media.I. The Products of Electrolysis of Monosaccharides", Can. J. Chem., 47 (3), 417–421 (1969).

*Primary Examiner*—John F. Niebling
*Assistant Examiner*—Steven P. Marquis
*Attorney, Agent, or Firm*—Leydig, Voit & Mayer

[57] ABSTRACT

A method has been developed of the production of D-arabinose as a base material in the production of vitamin B2. The substance of the method rests in that the solution of a salt of D-gluconic acid is subject to direct electrochemical degradation oxidation by the action of direct current and with the aid of the fluidized bed anode with a layer of electrically conductive particles kept in suspension by the flow of the reaction mixture. Graphite or coke is used as electrically conductive particles.

2 Claims, 1 Drawing Sheet

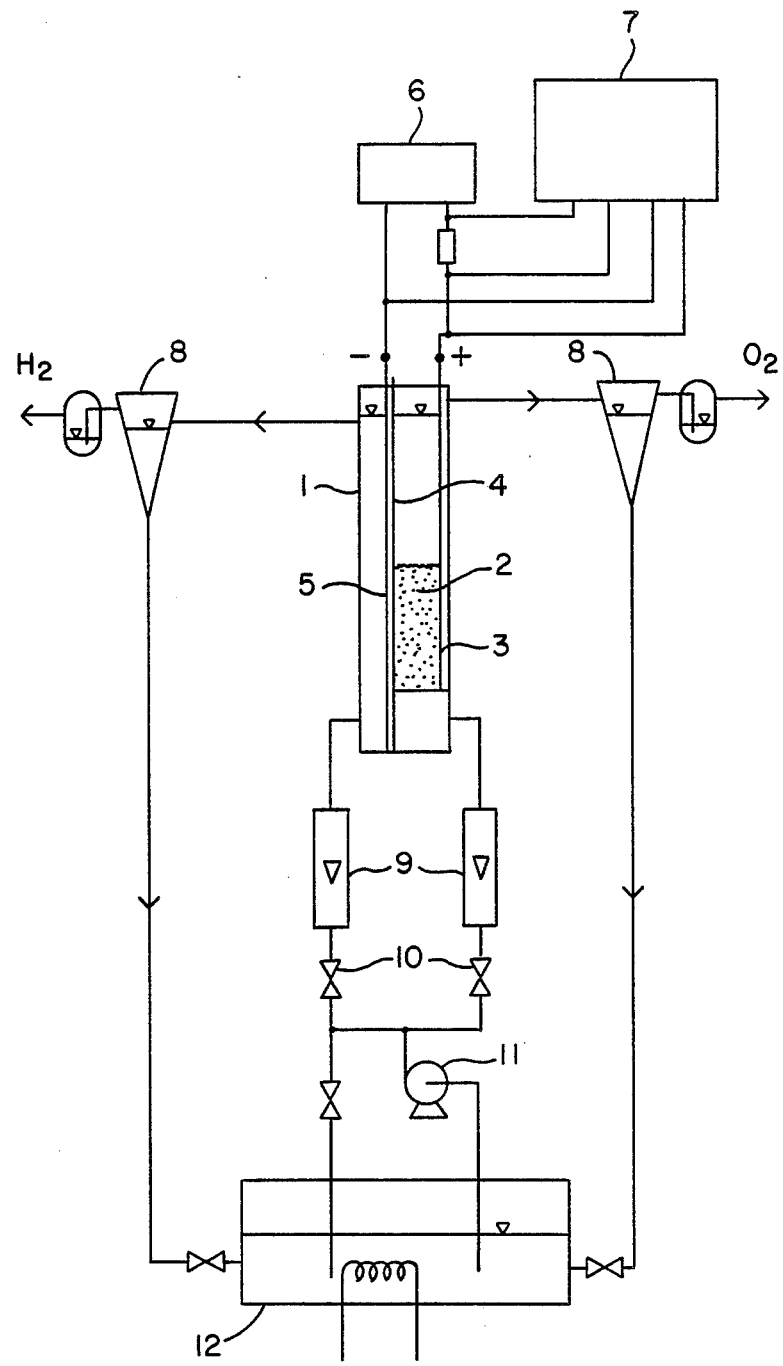

METHOD OF PRODUCTION OF D-ARABINOSE

BACKGROUND OF THE INVENTION

The invention relates to the method of production of D-arabinose by direct electrochemical degradation oxidation of a salt of D-gluconic acid.

D-arabinose is an important monosacharide utilized primarily for production of D-ribose in the synthesis of vitamin B2, as a starting material in the production of arabinoxine, as culture medium, etc.

D-arabinose may be prepared by chemical or electrochemical methods causing shortening of the carbon chain by degradation oxidation of D-gluconic acid or its derivatives. A most frequent method utilizes hydrogen peroxide and the catalytic effect of ferric ions (H. C. Fletcher, H. W. Dichl, C. S. Hudson: J. Amer. Chem. Soc. 72,4546, 1950). Industrially best developed method makes use of the oxidation degradation of sodium D-gluconate by the solution of sodium hypochlorite in acid solution (Wolf R., Merck Patent GmbH Federal Republic of German 2,923,267 (1980), 2,923,268 (1980), Eur. Pat. Appl. 20,959 (1981)). Substantial disadvantage of chemical methods utilizing oxidizing agents in at least stoichiometric amount is the high costs of subsequent separation of e.g., 1.5 kg of NaCl per 1 kg of d-arabinose produced during hypochlorite oxidation, or separation of cupric ions, whose presence is intolerable for pharmaceutical production of vitamin B2.

Indirect electrochemical degradation oxidation of D-gluconic acid requires, in comparison with the chemical methods, only a fraction of the stoichiometric amount of the oxidizing agent electrochemically regenerated during the reaction. Use of ceric salts for indirect oxidation is subject of Japanese patent Nos. (58-39695 (1983), 56-013613 (1981)). A drawback of this method is the costly separation of ceric salts from the product and very low specific production capacity of conventional plate electrolyzers.

This drawback becomes even more manifest in case of direct electrochemical degradation oxidation of D-gluconic acid. In the literature presented results (G. W. Hay, F. Smith, J. Can. of Chem. 47 (1969)417) of direct degradation oxidation of D-glucose in nonaqueous solution indicate only 12.4% of D-arabinose and low selectivity of the reaction. The low yield of this slow reaction is the consequence of small electrode area of the conventional parallel plate laboratory electrolyzer and low current denisty admissible for the given reaction. From the standpoint of industrial utilization this method in conjunction with the conventional electrolyzers is economically unfeasible.

Low interfacial area of electrodes per unit volume of the conventional plate electrolyzers leads in industrial practice to voluminous apparatuses and high investment costs. Also the running costs and the costs of subsequent separation of D-arabinose are high due to the very low yield and selectivity of the reaction.

SUMMARY OF THE INVENTION

The above disadvantages of chemical and electromchemical methods of production of D-arabinose are removed by the method according to this invention consisting in that the solution of a salt of D-gluconic acid is subject to direct electrochemical degradation oxidation by the action of direct current with the use of fluidized bed anode with a layer of electrically conductive particles kept in suspension by the flow of the reaction mixture. Graphite or coke is used as electrically conductive particles.

BRIEF DESCRIPTION OF THE DRAWINGS

The FIGURE schematically depicts the electrochemical degradation oxidation reaction of the present invention.

DETAILED DESCRIPTION OF THE PREFERRED EMBODIMENTS

An advantage of the method according to the invention is the radical innovation of the method of production of D-arabinose since no catalysts nor oxidizing agents are added to the reaction mixture that would have to be subsequently removed by costly separation techniques. Even traces of catalysts that is ions of copper or cerium in this case are inacceptable for pharmaceutical purposes.

Another advantage of the method according to the invention is that the fluidized bed anode permits work with high apparent current densities related to a unit area of membrane separating the cathode and anode chambers, while the real current densities, related to a unit area of the surface of the fluidized bed anode, are low. Degraduation oxidation therefore takes place with high selectivity and high yield. For the same reason the time-space efficiency of the method according to the invention is extremely high and the volume of the reactor per unit of production capacity is very low. The investment costs are therefore low. Thanks to the high current efficiency the energy requirements of the method are also low simultaneously with low maintanance costs. The cations of the salt of gluconic acid take the form of carbonates which can be easily separated by well-known techniques.

The utilization of the method according to the invention is demonstrated on the following examples describing, for clarity, first the equipment and further the realization of the invention, which, however, do not confine its protection.

The attached figure shows the scheme of the equipment used for the production of D-arabinose according to the invention.

A substantial part of the apparatus is an electrochemical reactor 1 with the fluidized bed anode 2. The fluidized bed anode 2 comprises a layer of graphite particles 0.0008 m in diameter kept in suspension by the flowing solution. Direct current is fed into the layer by means of a graphite current feeder 3. Cathode 5 is manufactured of an expanded stainless steel sheet. Porous membrane 4, made of PVC, 84 square centimeters in area, divides the electrochemical reactor 1 into the anode and cathode chambers.

A source of direct current 6 is connected to the clamps of the electrochemical reactor and a chart recorder 7 records the current passing through the reactor 1 as well as the voltage on the clamps. Part of the liquid loop is a thermostated storage tank 10, flowmeters 9 and cyclones 8 disengaging the hydrogen or oxygen bubbles from the electrolyte leaving the cathode and the anode chambers of the reactor 1 respectively.

EXAMPLE 1

0.002 cubic meters of solution containing 1.56 mole of sodium D-gluconate was thermostated at 40 degrss Celsius in the storage tank. After setting the flow rates of the solution at 0.05 kg/s and 0.0083 kg/s through the anode and the cathode chamber respectively, direct current at 10 A was fed into the clamps of the reactor until reaching 1.55 times the theoretical consumption of the current. 10 A corresponds to an apparent current density 1190 amperes per square meter of the area of porous membrane. The current was then disconnected and the composition of the reaction mixture was analyzed by high performance liquid chromatography. The reason mixture contained 0.185 kg D-arabinose, with corresponding conversion 78.9% by mass, related to the amount of theoretically obtainable D-arabinose and only 0.002 kg of D-erythrose, with corresponding selectivity of the reaction 98.9%. The rest was unreacted sodium D-gluconate and sodium carbonate originated during the reaction.

The above data correspond to the specific production capacity of 71 kg of D-arabinose per hour per cubic meter of the volume of the fluidized bed anode or 20 kg of D-arabinose per hour per cubic meter of the volume of the whole reactor, i.e. cathode and anode chambers and the liquid distribution block. The corresponding power consumption was 10 kWh per kg of D-arabinose.

EXAMPLE 2

Conditions and arrangement as in example 1. Coke was used instead of the graphite particles and potassium D-gluconate was used as a starting material. The achieved conversion was 74.8% with the selectivity 98%.

What is claimed is:

1. A method of production of D-arabinose by direct electrochemical degradation oxidation of salts of D-gluconic acid characterized by that the solution of the salt of D-gluconic acid is subjected to direct electrochemical degradation oxidation by direct current with the use of fluidized bed anode with a layer of electrically conductive particles kept in suspension by the flow of the reaction mixture.

2. A method of production of D-arabinose of claim 1 characterized by that the electrically conductive particles are graphite or coke.

* * * * *